United States Patent [19]

Kane

[11] Patent Number: 5,152,287
[45] Date of Patent: Oct. 6, 1992

[54] CROSS-LINKED FLUORINATED POLYMERS FOR USE IN GAS SENSORS

[75] Inventor: James A. Kane, Miami, Fla.

[73] Assignee: Cordis Corporation, Miami Lakes, Fla.

[21] Appl. No.: 568,275

[22] Filed: Aug. 15, 1990

[51] Int. Cl.$^5$ .................................. A61B 5/00
[52] U.S. Cl. .................................. 128/634; 128/636; 264/415; 356/39
[58] Field of Search .................. 128/634-636; 204/403, 415; 356/39, 40; 435/817; 436/163

[56] References Cited

U.S. PATENT DOCUMENTS

| | | | |
|---|---|---|---|
| 4,511,209 | 4/1985 | Skutnik | 350/96.34 |
| 4,682,895 | 7/1987 | Costello | 356/402 |
| 4,743,629 | 5/1988 | Karakelle et al. | 521/175 |
| 4,785,814 | 11/1988 | Kane | 128/634 |
| 4,800,886 | 1/1989 | Nestor | 128/634 |
| 4,842,783 | 6/1989 | Blaylock | 264/1.4 |
| 4,906,249 | 3/1990 | Fogt et al. | 128/636 |
| 4,959,130 | 9/1990 | Josowicz et al. | 204/32.1 |

FOREIGN PATENT DOCUMENTS

| | | | |
|---|---|---|---|
| 252578 | 1/1988 | European Pat. Off. | 128/634 |
| 352610 | 1/1990 | European Pat. Off. | 128/634 |
| 56-747 | 4/1982 | Japan | 204/415 |
| 8303344 | 10/1983 | World Int. Prop. O. | 128/634 |

OTHER PUBLICATIONS

Seitz article, "Chemical Sensors Based on Fiber Optics", *Analytical Chemistry*, vol. 56, No. 1, Jan., 1984.

*Primary Examiner*—C. Fred Rosenbaum
*Assistant Examiner*—Mark O. Polutta
*Attorney, Agent, or Firm*—Lockwood, Alex, FitzGibbon & Cummings

[57] ABSTRACT

A chemical sensor matrix is provided for use in medical, biological and industrial applications. The gas sensor includes a cross-linked fluoropolymer matrix of a composite having a gas-sensitive indicator within the matrix. The composite includes a highly fluorinated monofunctional acrylate monomer and a multifunctional acrylate cross-linking agent. Gas-sensitive indicator components which are suitable for detecting gases such as oxygen, carbon dioxide and the like represent indicators suitable for incorporation into the cross-linked fluoropolymer matrix.

23 Claims, 1 Drawing Sheet

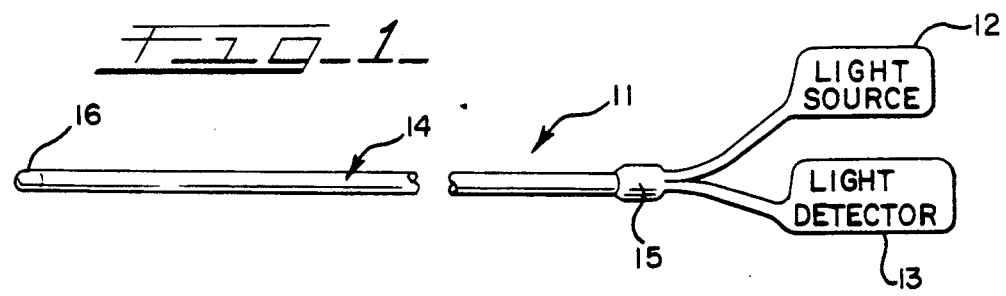
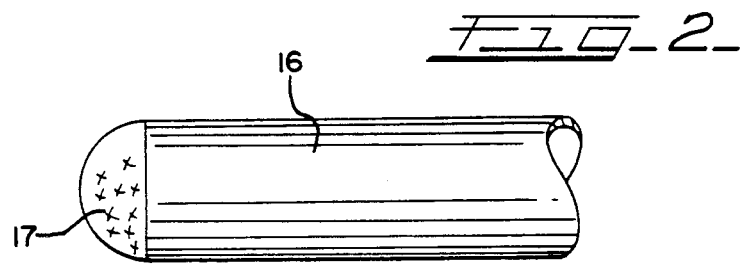
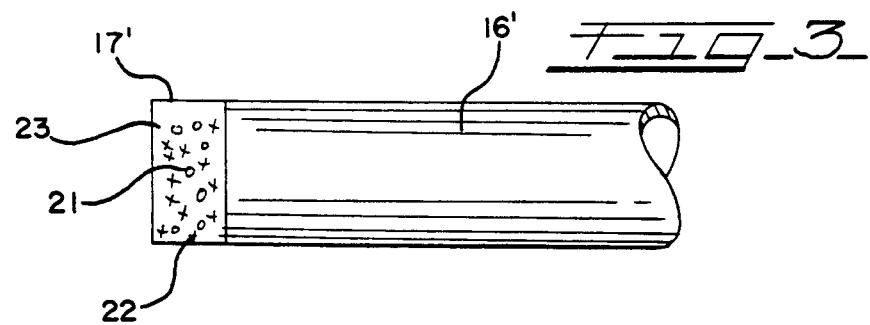
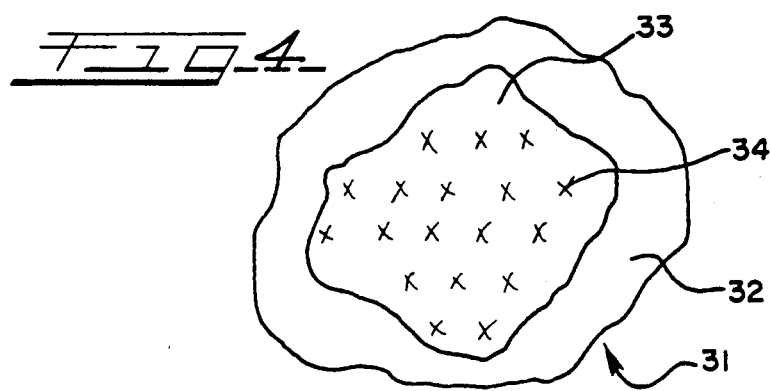

CROSS-LINKED FLUORINATED POLYMERS FOR USE IN GAS SENSORS

DESCRIPTION

1. Background and Description of the Invention

The present invention generally relates to cross-linked fluorinated polymers for use in chemical sensors for monitoring, detecting and/or measuring gas parameters at locations remote from detection instrumentation. More particularly, the invention relates to cross-linked fluorinated polymers for use in gas sensors that are useful as membranes, microparticles and the like for gas sensors such as those of the fiber optic type, the electrochemical type, or the like. The cross-linked fluorinated polymers for gas sensors are a matrix of a composite which includes a highly fluorinated monofunctional acrylate and a multi-functional acrylate cross-linking agent, with a gas indicator being included within the matrix.

Chemical sensors are generally known for use in a wide variety of areas such as medicine, scientific research, industrial applications and the like. Fiber optic and electrochemical approaches are generally known for use in situations where it is desired to detect and/or measure the concentration of a parameter at a remote location without requiring electrical communication with the remote location. Structures, properties, functions and operational details of fiber optic chemical sensors can be found in U.S. Pat. No. 4,577,109, U.S. Pat. No. 4,785,814 and U.S. Pat. No. 4,842,783, as well as Seitz, "Chemical Sensors Based on Fiber Optics", *Analytical Chemistry*, Vol. 56, No. 1, January, 1984, each of which is incorporated by reference hereinto.

Publications such as these generally illustrate that it is known to incorporate a chemical sensor into a fiber optic waveguide, an electrochemical gas sensor or the like, in a manner such that the chemical sensor will interact with the analyte. This interaction results in a change in optical properties, which change is probed and detected through the fiber optic waveguide or the like. These optical properties of the chemical sensor compositions typically involve changes in colors or in color intensities. In these types of systems, it is possible to detect particularly minute changes in the parameter or parameters being monitored in order to thereby provide especially sensitive remote monitoring capabilities. Chemical sensor compositions that are incorporated at the distal end of fiber optic sensors are often configured as membranes that are secured at the distal tip end of the waveguide device or optrode.

Gas sensors of this general type are useful in monitoring gas concentrations such as oxygen, carbon dioxide and the like. Also, it is sometimes desirable to provide sensors that also monitor other parameters such as pH measurement. Ion concentrations can also be detected, such as potassium, sodium, calcium and metal ions.

A typical gas sensor device positions the sensor material at a generally distal location with the assistance of various different support means. Support means must be such as to permit interaction between the gas indicator and the substance being subjected to monitoring, measurement and/or detection. Known approaches in this regard include the use of permeable membranes and composites incorporating micro-encapsulation. With certain arrangements, it is desirable to incorporate membrane components into these types of devices. These membrane components must possess certain properties in order to be particularly advantageous. Many membrane materials have some advantageous properties but also have shortcomings. Generally speaking, the materials must be biocompatible, they must be permeable to the gas being monitored, and they must be capable of supporting the gas-sensitive indicator, while at the same time possessing the strength adequate to permit maneuvering of the device without concern about damage to the gas sensor. It is also desirable to have these materials be photocurable in order to facilitate locating the gas sensor composite on the device.

In summary, the present invention recognizes that certain polymer compositions are particularly suitable for use as membranes and membrane-like components which incorporate gas-sensitive indicators in forming the active gas sensor component of a gas sensor device such as those incorporating fiber optic or electrochemical technology. The polymer composition contains a highly fluorinated monofunctional acrylate and a multi-functional acrylate cross-linking agent in order to provide a composite within which a gas-sensitive indicator is incorporated. When cured, the composite is gas permeable, hydrophobic, biocompatible or non-toxic and is miscible with the gas-sensitive indicator. The cured polymer has a mechanical strength that is superior, for example, to silicone with respect to tear resistance. The polymer materials are also photocuring which enables selective deposition on the active portion of the gas sensor device. The polymer is also non-thrombogenic or at least non-thrombus adherent, and it exhibits immunity to extraction of the gas-sensitive indicator. The composite, with the indicator incorporated therewithin, is cross-linked and cured into a fluoropolymer gas permeable matrix.

It is a general object of the present invention to provide an improved gas sensor.

Another object of the present invention is to provide an improved gas sensor having a polymer composition that has excellent optical clarity and is particularly suitable for supporting a gas-sensitive component such as an oxygen sensitive luminescent compound or the like.

Another object of the present invention is to provide an improved gas sensor device incorporating a matrix that is hard, biocompatible and non-extractable with respect to gas-sensitive indicators incorporated into the matrix polymer.

Another object of the present invention is to provide an improved gas sensor device having gas sensor means possessing properties which are especially advantageous for the gas sensor device.

Another object of this invention is to provide a gas sensor membrane which allows for a loading of a gas-sensitive indicator which is particularly high, for example greater than one percent by weight.

Another object of the present invention is to provide a polymer composite suitable for forming a variety of differently configured gas sensor structures, including monolithic membranes, composite membranes having both gas sensor and other parameter detection abilities, as well as for providing microparticles incorporating gas-sensitive indicators.

Another object of the present invention is to provide gas sensor polymers which are rigid enough to resist swelling but not overly rigid so as to shatter in response to ionic solution equilibration phenomena.

These and other objects, features and advantages of this invention will be clearly understood through a consideration of the following detailed description.

BRIEF DESCRIPTION OF THE DRAWINGS

In the course of this description, reference will be made to the attached drawings, wherein:

FIG. 1 is a generally schematic view of a chemical sensor device according to the present invention which is incorporated in a fiber optic gas sensor device;

FIG. 2 is an enlarged, detail and generally schematic view of the distal end portion of a gas sensor device generally in accordance with FIG. 1 and incorporating a monolithic cross-linked fluorocarbon polymer according to the present invention;

FIG. 3 is a view similar to FIG. 2 but illustrating a composite membrane arrangement; and FIG. 4 is a schematic view illustrating a microparticle of the type that can be incorporated into gas sensor membranes.

DESCRIPTION OF THE PARTICULAR EMBODIMENTS

The composites according to the present invention are compositions of fluorinated acrylates which, when cured, form membranes with mechanical, chemical and optical properties useful in fiber optic, as well as electrochemical, gas sensors and the like. For purposes of illustration, FIG. 1 shows a typical fiber optic gas sensor arrangement. The illustrated device 11 includes a light source 12 for directing probe radiation into the device, as well as a light detector 13 for sensing and detecting radiation from the device. Device 11 includes one or more optical fibers 14 that are joined to light source 12 and to light detector 13 through a suitable junction assembly 15 at a location which is proximal of the distal end portion 16 of the optical fiber 14. As is generally known, each optical fiber 14 includes a core surrounded by a cladding or covering.

Distal end portion 16 has a distal tip 17 which is a monolithic cross-linked fluorocarbon polymer membrane. With more particular reference to the distal tip 17, the fluorocarbon polymer membrane includes a gas sensitive indicator matrix. The fluorocarbon polymer membrane securely supports the gas-sensitive indicator to provide a matrix which undergoes a known change in color or color intensity or other property, which change is observed by the light detector 13 in a manner generally known in the art.

With the embodiment illustrated in FIG. 3, a distal end portion 16' has a distal tip 17'. The tip 17' is a composite membrane suitable for multifunctional monitoring, such as for monitoring pH conditions or the like and gas concentrations. Microparticles 21 of cross-linked fluorocarbon polymer and gas-sensitive indicator matrix (which can be chemically the same as the distal tip 17 of the embodiment shown in FIG. 2) are included within the composite membrane at the distal tip 17'. Also included are other indicator components 22 such as fluorescent pH indicators. Both the gas sensor microparticles 21 and the other indicators 22 are encapsulated within a known type of gas and ion permeable hydrophilic polymer 23 which provide needed support for the microparticles therewithin.

FIG. 4 illustrates another type of microparticle. Microparticles will have a nominal diameter of between about 1 and about 100 microns. Microparticles such as these can be incorporated, for example, within a polymer such as the gas and ion permeable hydrophilic polymer 23 shown in FIG. 3. The microparticle of FIG. 4 is generally designated as 31. It includes an outer layer or casing component of cross-linked fluoropolymer 32 in accordance with this invention in order to provide gas monitoring capabilities to the microparticle 31. Included within the fluoropolymer casing component 32 is a hydrophilic polymer 33 having other indicator components 34, such as pH indicators, dispersed therewithin. A gas such as carbon dioxide or the like will penetrate into the cross-linked fluoropolymer and be detected by the component 34, while oxygen will be detected by the oxygen indicator components.

With more particular reference to the gas sensor materials such as those illustrated at the distal tips 17 and 17' of the drawings, the cross-linked fluorocarbon polymers are composites of fluorinated acrylates which cure into membranes or microparticles or the like which possess the advantageous properties according to the present invention. Included is a highly fluorinated monofunctional acrylate monomer and a multifunctional acrylate cross-linking agent. An ultraviolet and/or visible photoinitiator may be included when desired. Also included is a gas-sensitive component in order to impart gas sensitivity to the gas permeable membrane or microparticle.

Typically, the composition from which the membrane or microparticle is formed will include the highly fluorinated monofunctional acrylate monomer as its major component. The multifunctional acrylate cross-linking agent is typically the component having the second greatest concentration. For example, the fluorinated acrylate monomer will be present at between about 60 and about 90 weight percent of the composition, preferably between about 75 and about 85 weight percent. The monofunctional acrylate cross-linking agent will typically be present between about 10 and about 40 weight percent, preferably between about 15 and about 25 weight percent of the composition. When included, the photoinitiator will be present at customary levels, typically substantially below 1 weight percent of the total composition. Most gas-sensitive compounds will be present at between about 0.5 and about 3 weight percent of the composition, most preferably at approximately 1% of the composition.

With more particular reference to the highly fluorinated monofunctional acrylate monomer, these are discussed generally in U.S. Pat. No. 4,511,209, the subject matter thereof being incorporated by reference hereinto. Generally speaking, these highly fluorinated acrylate monomers are of the formula:

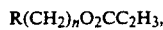

$$R(CH_2)_n O_2 CC_2 H_3,$$

wherein R is $X(CF_2)_m$, where m is from 3 to 12, inclusive, X is H or F; and wherein n is 1, 2 ... 3 m.

These acrylate monomers are highly fluorinated to the extent that a minimum of three C-F bonds, or 25% or more of the C-H bonds have been replaced with C-F bonds, whichever alternative provides the higher number of C-F bonds.

These highly fluorinated acrylate monomers can also include substituents in addition to those specified in the preceding formula, for example sulfonamido groups and nitrogen groups. An exemplary formula in this regard is:

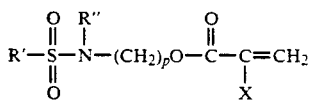

wherein R' is $C_MF_{2M+1}$, where M is 2 or more; wherein R" is $CH_3$, $C_2H_5$ ... $C_4H_9$; and wherein X is H or $CH_3$.

Exemplary highly fluorinated acrylate monomers include 2-(N-butylperfluorooctanesulfonamido) ethyl acrylate, 2-(N-ethylperfluorooctanesulfonamido) ethyl acrylate and the perfluorooctyl acrylate available from 3M Chemicals under the designation Monomer No. L-9186. Other highly fluorinated acrylate monomers include trihydroperfluoroheptyl acrylate, trihydroperfluoroundecyl acrylate and nonahydroperfluorodecyl acrylate.

Concerning the multifunctional acrylate cross-linking agent, preferably it should be trifunctional or of greater functionality. Exemplary triacrylates in this regard include trimethylol propane triacrylate and 2-ethyl-2-(hydroxymethyl)-1,3-propanediol triacrylate and the like.

When included, the photosensitizers or photoinitiators are reactive compounds which are generally well-known in the art. Included are diethoxyacetophenone; certain propanones; methyl, ethyl, propyl or isobutyl ethers of benzoin and other analogs; and 2,2-dimethoxy, 2-phenyl-acetophenone.

Thermally activated free-radical initiators can be utilized particularly when preparing microparticles. Typically not greater than 1 weight percent of potassium persulfate can be added. Other types of initiators can be utilized. Included are benzoyl peroxide, azobis isobutyronitrile, ammonium persulfate, and other organic peroxides, azo compounds and redox reagents.

Gas-sensitive components which are incorporated into the membrane, microparticle or the like in accordance with this invention include components sensitive to gases, the most common being oxygen and carbon dioxide gases. An exemplary type of sensor is a transition metal complex such as tris(4,7-diphneyl 1,10-phenanthroline) ruthenium II chloride. When composite microparticles or the like are to be formed, indicators other than gas-sensitive indicators can also be included. For example, a known indicator is a fluorescent pH indicator such as hydroxypyrene trisulfonic acid on anion exchange resin. Buffer solutions can also be included.

With further reference to the concentration of the gas-sensitive sensor component within the composition, its upper limit typically will be the point of saturation of the gas sensor material in the composite composition. Incorporation of the gas-sensitive sensor material into the composition can be facilitated by solvent incorporation procedures. For example, the desired concentration of gas indicator material can be dissolved in a common solvent such as methanol and then mixed with the monomer solution. If desired, the methanol can then be removed by a simple vacuum distillation procedure, such as running the composition through a rotary type evaporator.

Depending upon the particular embodiment, it may be necessary to adhere the membrane formed by the composition to a glass surface, such as when the membrane is adhered to an optical fiber. In these instances, it is typically necessary to prime the glass prior to deposition of the sensing membrane thereonto. Typical glass primers in this regard include gamma-methacryloxypropyl trimethoxysilane.

When the composition is used for forming a sensing membrane or optrode at the end of an optical fiber, this can be accomplished by dipping the distal tip into the monomer solution containing the gas sensitive component and taking suitable steps to cure and cross-link the solution with the gas-sensitive component therewithin. Once thus cured, the gas sensor thus formed at the distal tip is preferably cleaned of residual unreactive monomers by rinsing with a solvent such as acetone. When the composition is used for forming microparticles which can be dispersed into other polymers and the like to define a gas sensor, the microparticles can be prepared by polymerizing within a fluid such as water and collecting the particles thus formed. Alternatively, the composition can be cast and polymerized between opposing sheets, such as between glass plates. After the plates are removed, the polymer sheet can be ground into microparticles suitable for dispersion as desired. One advantage of utilizing the microparticle approach is that it is easier to form relatively thick gas sensors, such as ones on the order of up to 1 mm in thickness because the formed microparticles are simply incorporated into a polymer of the desired thickness to make the gas sensor.

Membranes and microparticles prepared according to this invention have the important feature and advantage of exhibiting optical clarity, while at the same time being resistant to damage by physical contact with other surfaces. They are also biocompatible and highly permeable to gases such as oxygen which are to be sensed by the gas sensitive component with the matrix. The membranes also have non-extractable properties such that extraction of components thereof will be minimized if not completely avoided when the gas sensor device is in use within the body or the like. The membranes or microparticles formed according to the invention are particularly useful for optical oxygen sensors that are intended to be used in the tissues of non-heparinized patients. Even in these environments, the invention provides a gas sensor exhibiting a low degree of thrombogenicity and/or low thrombus adherence. The invention also permits a relatively high loading of the gas-sensitive component, for example on the order of or in excess of 1 weight percent of the total composition.

EXAMPLE 1

A composite solution was prepared by combining 80.0 weight percent of 2-(N-butylperfluorooctanesufonamido)ethyl acrylate monomer together with 19.9 weight percent of trimethylol propane triacrylate cross-linking agent. Also included was 0.1 weight percent of diethoxyacetophenone photoinitiator. It is desirable that the concentration of the initiator be minimized so as to avoid free radical decomposition of the complex. Based on the total weight of the composition being prepared, also added was about 1 weight percent of a gas-sensitive indicator, tris(4,7-diphenyl 1,10-phenanthroline) ruthenium chloride in methanol. The distal end tip of an optical fiber was dipped into the monomer composition thus formed. Thereafter, this distal tip end was placed into a stream of nitrogen gas in order to de-oxygenate the composition. Curing then was completed by pumping the distal end tip of the fiber with light from a mercury arc lamp. The membrane thus formed was optically clear, hard, biocompatible, highly oxygen permeable, and non-extractable with respect to the indicator of this membrane.

EXAMPLE 2

A photopolymerizing monolithic fluoropolymer/dye matrix is prepared from a monomer solution composition combined with an oxygen indicator. The monomer solution composition or composite includes 79.0 weight percent of Monomer No. L-9186 from 3M Chemicals, which is a perfluorooctylacrylate, together with 19.9 weight percent of 2-ethyl-2-(hydroxymethyl)-1,3-propanedioltriacrylate cross-linking agent and 0.1 percent diethoxyacetophenone photoinitiator. The oxygen indicator is 1% by weight of tris(4,7-diphenyl 1,10-phenanthroline) ruthenium II chloride. Dipping and curing generally in accordance with Example 1 results in the preparation of an optical waveguide having an oxygen sensor membrane at its distal tip.

EXAMPLE 3

A photopolymerizing monolithic fluoropolymer/dye matrix was prepared from a monomer solution composition combined with an oxygen indicator. The monomer solution composition or composite included 79.0 weight percent 2-(N-ethylperfluorooctanesulfonamido)ethyl acrylate monomer. The oxygen indicator used was 1% by weight of tris(4,7-diphenyl 1,10-phenanthroline) ruthenium chloride. Dipping and curing generally in accordance with Example 1 resulted in the preparation of an optical waveguide having an oxygen sensor membrane at its distal tip which was optically clear and exhibited good hardness without brittleness.

EXAMPLE 4

Oxygen-sensitive microparticles were prepared from a monomer solution composition including an oxygen indicator. The composition included 79.0 weight percent of 2-(N-butylperfluorooctanesulfonamido)ethyl acrylate, 20.0 weight percent of 2-ethyl-2-(hydroxymethyl)-1,3-propanediol triacrylate monomer cross-linking agent, and 1.0 weight percent of tris(4,7-diphenyl 1,10-phenanthroline) ruthenium chloride.

A glass-lined vessel was charged with 100 parts of distilled water. This water was boiled in order to expel dissolved air inasmuch as oxygen will inhibit polymerization. The boiled water was then blanketed with nitrogen gas. One hundred parts of the monomer solution composition was added to the boiled water, and the resultant mixture was stirred. The temperature of the stirred solution was adjusted to 50° C., and 0.5 part of potassium persulfate, a thermally activated free-radical initiator, was added. Heating and stirring were continued for 4 hours under a slight positive nitrogen pressure. Hard, clear, orange colored cross-linked particles were filtered from the solution using a Whatman No. 2 filter, which particles were washed repeatedly with acetone to remove residuals. These microparticles thus formed were incorporated into a gas and ion permeable hydrophilic polymer, poly(hydroxyethyl) methacrylate. Also incorporated into the hydrophilic polymer was a fluorescent pH indicator, hydroxypyrene trisulfonic acid anion exchange resin. A composite membrane resulted which was sensitive to both pH and oxygen concentration.

It will be understood that the embodiments of the present invention which have been described are illustrative of some of the applications of the principles of the present invention. Numerous modifications may be made by those skilled in the art without departing from the true spirit and scope of the invention.

I claim:

1. A gas sensor device comprising:

an optical waveguide having a distal end portion for monitoring a gas component within a bloodstream or the like, said optical waveguide further including a proximal end portion for communication with means for receiving a signal from said distal end portion;

said distal end portion has gas sensor means including a cross-linked fluoropolymer matrix having a gas-sensitive indicator therewithin; and said matrix is a composite formed by cross-linking a composition including between about 60 and about 90 weight percent of a highly fluorinated monofunctional acrylate monomer and between about 10 and about 40 weight percent of a multifunctional acrylate cross-linking agent, all weight percentages being based on the total weight of the composition, wherein said highly fluorinated monofunctional acrylate monomer is a component having a formula $R(CH_2)_nO_2CC_2H_3$, wherein R is $X(CF_2)_m$, where m is from 3 to 12, inclusive, X is H or F; and wherein n is 1, 2 ... 3 m, or a formula:

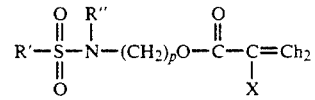

wherein R' is $C_MF_{2M+1}$, where M is 2 or more;
wherein R" is $CH_3, C_2H_5 \ldots C_4H_9$; and wherein X is H or $CH_3$, and
wherein said multifunctional acrylate cross-linking agent is a triacrylate or an acrylate of greater acrylate functionality.

2. The device according to claim 1, wherein said gas sensor means is a substantially monolithic membrane which is a cross-linked matrix of said composite and said indicator.

3. The device according to claim 1, wherein said gas sensor means includes a gas and ion permeable hydrophilic polymer having therewithin microparticles of said cross-linked fluoropolymer matrix.

4. The device according to claim 1, wherein said gas sensor means includes a gas and ion permeable hydrophilic polymer having therewithin microparticles of said cross-linked fluoropolymer matrix and of a fluorescent indicator for a parameter other than that detected by said gas-sensitive indicator.

5. The device according to claim 1, wherein said gas sensor means includes microparticles of said cross-linked fluoropolymer matrix, and said microparticles encapsulate a hydrophilic polymer having therewithin an indicator different from said gas-sensitive indicator.

6. The device according to claim 1, wherein said composite further includes not greater than about 1 weight percent of a photoinitiator.

7. The device according to claim 1, wherein said monomer is present at between about 75 and about 85 weight percent, based on the total weight of the composition.

8. The device according to claim 1, wherein said gas-sensitive indicator is a transition metal complex which is sensitive to oxygen or carbon dioxide.

9. A gas sensor device comprising:

an electrochemical gas sensor including gas sensor means for monitoring a gas component within a patient or the like;

said gas sensor means includes a gas-sensitive indicator within a cross-linked fluoropolymer matrix; and said matrix is a cross-linked composite of a composition including between about 60 to about 90 weight percent of a highly fluorinated monofunctional acrylate monomer and between about 10 and about 40 weight percent of a multifunctional acrylate cross-linking agent, all weight percentages being based on the total weight of the composition, wherein said highly fluorinated monofunctional acrylate monomer is a component having a formula $R(CH_2)_nO_2CC_2H_3$, wherein R is $X(CF_2)_m$, where m is from 3 to 12, inclusive, X is H or F; and wherein n is 1, 2 ... 3 m, or a formula:

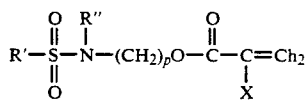

wherein R' is $C_MF_{2M+1}$, where M is 2 or more;
wherein R" is $CH_3$, $C_2H_5$ ... $C_4H_9$; and wherein X is H or $CH_3$, and
wherein said multifunctional acrylate cross-linking agent is a triacrylate or an acrylate of greater acrylate functionality.

10. The gas sensor device according to claim 9, wherein said composite further includes not greater than about 1 weight percent of a photoinitiator.

11. The gas sensor device according to claim 9, wherein said monomer is present at between about 75 and about 85 weight percent, based on the total weight of the composition.

12. A cross-linked gas permeable membrane for a gas sensor device, comprising:

a composite including a highly fluorinated monofunctional acrylate monomer and a multifunctional acrylate cross-linking agent, said composite further having incorporated therewithin a gas-sensitive indicator component;

wherein said highly fluorinated monofunctional acrylate monomer is a component having a formula $R(CH_2)_nO_2CC_2H_3$, wherein R is $X(CF_2)_m$, where m is from 3 to 12, inclusive, X is H or F; and wherein n is 1, 2 ... 3 m, or a formula:

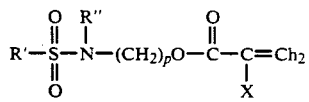

wherein R' is $C_MF_{2M+1}$, where M is 2 or more;
wherein R" is $CH_3$, $C_2H_5$ ... $C_4H_9$; and wherein X is H or $CH_3$, and
wherein said multifunctional acrylate cross-linking agent is a triacrylate or an acrylate of greater acrylate functionality; and
said composite and said indicator incorporated therewithin had been cross-linked and cured into a cross-linked fluoropolymer gas permeable component matrix.

13. The membrane according to claim 12, wherein said membrane includes a hydrophilic polymer having dispersed therewithin microparticles of said cross-linked fluoropolymer gas permeable component.

14. The membrane according to claim 12, wherein said membrane includes a gas and ion permeable hydrophilic polymer having dispersed therewithin microparticles of said cross-linked fluoropolymer component and a fluorescent indicator for a parameter other than that detected by said gas-sensitive indicator.

15. The membrane according to claim 12, wherein said monomer is present at between about 75 and about 85 weight percent, based on the total weight of the composition.

16. The membrane according to claim 12, wherein said gas-sensitive indicator is a transition metal complex which is sensitive to oxygen or carbon dioxide.

17. The membrane according to claim 12, wherein said monomer is selected from the group consisting of 2-(N-butylperfluorooctanesulfonamido) ethyl acrylate, 2-(N-ethylperfluorooctanesulfonamido) ethyl acrylate, perfluorooctyl acrylate, trihydroperfluoroheptyl acrylate, trihydroperfluoroundecyl acrylate, and nonahydroperfluorodecyl acrylate.

18. A cross-linked gas permeable microparticle for use within a gas sensor device, comprising:

a composite including a highly fluorinated monofunctional acrylate monomer and a multifunctional acrylate cross-linking agent, said composite further having incorporated therewithin a gas-sensitive indicator component;

wherein said highly fluorinated monofunctional acrylate monomer is a component having a formula $R(CH_2)_nO_2CC_2H_3$, wherein R is $X(CF_2)_m$, where m is from 3 to 12, inclusive, X is H or F; and wherein n is 1, 2 ... 3 m, or a formula:

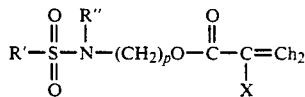

wherein R' is $C_MF_{2M+1}$, where M is 2 or more;
wherein R" is $CH_3$, $C_2H_5$ ... $C_4H_9$; and wherein X is H or $CH_3$, and
wherein said multifunctional acrylate cross-linking agent is a triacrylate or an acrylate of greater acrylate functionality; and
said composite and said indicator incorporated therewithin had been crosslinked and cured into a crosslinked fluoropolymer gas permeable microparticle matrix.

19. The microparticle according to claim 18, wherein said microparticle was formed by polymerizing said monomer, cross-linking agent and indicator component within a fluid.

20. The microparticle according to claim 18, wherein said microparticle was formed by polymerizing said monomer, cross-linking agent and indicator component between opposing plates to form a polymer sheet, removing the polymer sheet from the plates, and grinding the polymer sheet into microparticles 21. The microparticle according to claim 18, wherein said composite further includes not greater than about 1 weight percent of a photoinitiator.

22. The microparticle according to claim 18, wherein said monomer is present at between about 75 and about 85 weight percent, based on the total weight of the composition.

23. The microparticle according to claim 18, wherein said monomer is selected from the group consisting of 2-(N-butylperfluorooctanesulfonamido) ethyl acrylate, 2-(N-ethylperfluorooctanesulfonamido) ethyl acrylate, perfluorooctyl acrylate, trihydroperfluoroheptyl acrylate, trihydroperfluoroundecyl acrylate, and nonahydroperfluorodecyl acrylate.

* * * * *